United States Patent [19]

Tzodikov et al.

[11] 4,358,434
[45] Nov. 9, 1982

[54] METHOD, COMPOSITION AND KIT FOR STABILIZING RADIOLABELED COMPOUNDS

[75] Inventors: Nathan R. Tzodikov, Milton; Robert E. O'Brien, Belmont, both of Mass.

[73] Assignee: New England Nuclear Corporation, Boston, Mass.

[21] Appl. No.: 105,272

[22] Filed: Dec. 19, 1979

[51] Int. Cl.$^3$ .................... A61K 43/00; A61K 49/00
[52] U.S. Cl. .......................... 424/1; 424/9; 521/25
[58] Field of Search .................. 424/1, 9; 521/25

[56] References Cited

U.S. PATENT DOCUMENTS

| 3,928,293 | 12/1975 | Crosby | 260/570.9 |
|---|---|---|---|
| 4,029,706 | 6/1977 | Crosby | 260/570.9 |
| 4,048,416 | 9/1977 | Axen et al. | 424/1 |
| 4,062,933 | 12/1977 | Wolfangel | 424/1 |
| 4,107,283 | 8/1978 | Pratt et al. | 424/1 |
| 4,115,540 | 9/1978 | Digenis et al. | 424/1 |
| 4,217,338 | 8/1980 | Quash | 424/1 |

FOREIGN PATENT DOCUMENTS

| 88780 | 12/1970 | German Democratic Rep. | 521/25 |
|---|---|---|---|
| 432218 | 6/1974 | U.S.S.R. | 521/25 |

OTHER PUBLICATIONS

Liebster et al., Radiation Biol., 1, 157–226 (1964).
Merrifield, J. Am. Chem. Soc., 85, 2149–2154 (1963).
Crowley et al., Accts. Chem. Res., 9, 135–144 (1976).

*Primary Examiner*—Christine M. Nucker
*Attorney, Agent, or Firm*—Sewall P. Bronstein; George W. Neuner

[57] ABSTRACT

A method and kit for stabilizing solutions of radiolabelled compound by the use of insoluble quaternary ammonium containing compounds. Also described are novel insoluble compounds having quaternary ammonium and sulfide groups for use in the present invention.

40 Claims, No Drawings

METHOD, COMPOSITION AND KIT FOR STABILIZING RADIOLABELED COMPOUNDS

BACKGROUND OF THE INVENTION

1. Field of the Invention

This invention relates to the stabilization of radiolabeled compounds, such as amino acids and nucleosides, and more particularly, to stabilization of such compounds without adulteration thereof.

2. Description of the Prior Art

An increasing number of radiolabeled compounds are being used in research, for medical diagnosis, and various other areas. However, the radiolytic decomposition of such compounds has been a constant problem. Without the addition of some type of stabilizer, a solution of such a compound may become unusable due to decomposition within a matter of weeks or less. This radiolytic decomposition of such compounds has been studied extensively. For example, the radiation chemistry of amino acids is reviewed in an article by J. Liebster and J. Kopeldova, *Radiation Biol.*, 1, 157 (1964). In spite of this knowledge, the stabilizers presently available suffer from the disadvantage of being soluble in the solutions used to store the radiolabeled compounds, thereby adulterating such solutions and the radiolabled compounds stored therein.

The synthesis and use of polystyrene supported reagents for solid phase peptide preparation is known in the prior art. R. B. Merrifield, *J. Am. Chem. Soc.*, 85, 2149 (1963); Crowley et al, *Accts. Chem. Res.*, 9, 135 (1976); G. R. Stark (1971), *Biochemical Aspects of Reactions on Solid Supports*, Academic Press, N.Y. U.S. Pat. Nos. 3,928,293 and 4,029,706 describe thiohydrocarbon polymers and their use as borane chelaters. However, neither the synthesis nor use of the compounds of the present invention is described in any of the above.

SUMMARY OF THE INVENTION

A method of stabilizing a solution of a radiolabeled compound comprising adding to such solution a substantially insoluble compound, preferably a resin, such as an ion exchange resin, containing a quaternary ammonium group.

DETAILED DESCRIPTION OF THE INVENTION

The substantially insoluble quaternary ammonium containing compounds of the present invention can be any of those well known in the prior art. A preferred class of such compounds is that prepared by attaching quaternary ammonium groups to an insoluble polystyrene-divinylbenzene copolymer backbone, e.g., a copolymer formed by copolymerizing about 1% to about 10% by weight of divinylbenzene with styrene. The preparation of such copolymers is well known in the prior art and they are sold commercially for use as anion exchange resins. Such commercially available copolymers are preferably treated by washing with ethanol and then methylene chloride, followed by drying before being employed to stabilize radiolabeled compounds.

The nitrogen of the quaternary ammonium group of the compounds of the present invention is preferably substituted by hydroxyalkyl or alkyl chains, preferably lower alkyl, and more preferably of from 1 to 5 carbon atoms.

The counterion (anion) of the quaternary compounds of the present invention can be any of those known in the prior art which do not significantly detract from the stabilization provided by the quaternary ammonium group. Preferred counterions are halides and alkyl carboxylate ions of one to five carbon atoms, such as formate and acetate. A particularly preferred counterion is chloride.

Particularly preferred for use in the present invention are novel compounds prepared by attaching a sulfide or thiol group to the stabilizing compounds described above. Preferred sulfide groups are those substituted by an alkyl group of one to five carbon atoms. Insoluble ammonium sulfide compounds have been found to be particularly effective in stabilizing solutions of radiolabeled compounds.

While any amount of the stabilizer compounds described above is beneficial in preventing the decomposition of radiolabeled compounds, it is preferred that the quaternary ammonium containing compound be present in molar excesses of nitrogen of between about $10^2$ and about $10^5$, more preferably between about $10^3$ and $10^4$, and most preferably about $10^4$. When a sulfide or thiol group is attached to the backbone, it is preferred that the sulfur be present in molar excesses between about $10^2$ and $10^5$, preferably between about $10^3$ and about $10^4$, and most preferably about $10^4$. By molar excess is meant, an excess of the respective atom, e.g., nitrogen, in the stabilizing compound over the equivalents of the radiolabeled compound.

The method of the present invention can be used with any of the solvents typically used to store radiolabeled compounds such as water, ethanol, mixtures of water and ethanol in any ratio, benzene, hexane, dilute mineral and organic acids, and other such solvents employed in the prior art.

The present invention can be used to prevent the decomposition of radiolabeled compounds, which have been labeled with any of the radionuclides used for such purposes, including tritium, carbon-14, phosphorus-32, phosphorus-33, sulfur-35, and the various radioisotopes of iodine, including iodine-125, and iodine-131.

The radiolabeled compound may be any of those subject to radiolytic decomposition, such as radiolabeled organic compounds. Examples of such organic compounds included amino acids such as lysine, tyrosine, phenylalanine, and tryptophan.

The stabilizing compounds are particularly effective with methionine and leucine. Other such organic compounds include peptides; nucleosides, such as thymidine and uridine; nucleotides, polynucleotides; lipids; steroids, and catecholamines.

Radiolabeled compounds are typically commercially distributed in closed vials containing a solution of the particular radiolabeled compound. The stabilizing compound can take various forms as long as it is maintained in contact with the solution of radiolabeled compound. An example of a possible form is solid beads which are added to a solution of the radiolabeled compound, in which case the solution would be removed from the stabilizing compound by decanting or withdrawing by means of a syringe. Another potential means of storage would be to provide the stabilizing compound in a form whereby the solution of the radiolabeled compound would be absorbed by the stabilizing compound. In such a case, the solution of radiolabeled compound would be eluted from the mass of stabilizing compound by use of a suitable solvent. Once separated, the solution of radiolabeled compound is used in the same manner as unstabilized solutions thereof.

The invention will be further clarified by a consideration of the following examples, which are intended to be purely exemplary of the use of the invention.

EXAMPLE I

Preparation of Polystyrene-divinylbenzene bound ammonium sulfide, chloride form

To a suspension of chloromethylated polystyrene copolymerized with 1% divinylbenzene (10 g, 42.5 milliequivalents chloride by analysis) in methylene chloride (200 ml) was added ethanethiol (15.7 ml, 213 mMol) and triethylamine (29.6 ml, 213 mMol). A slight yellow color began to develop after approximately 10 minutes and the mixture was allowed to stir for 60 hrs. under a nitrogen atmosphere. The resultant suspension was filtered through paper and continuously extracted with chloroform for 24 hrs., ethanol 3 hrs., then washed with chloroform (5×40 ml), ethanol (5×40 ml) and the white resin that remained was dried in a vacuum oven at 60° C./20 mm to leave 10 g of the ammonium sulfide polymer. The analysis of C, 71.18; H, 8.84; N, 215; S, 4.90; Cl, 5.26 indicates 1.53 mequivalents Sulfur/g, 1.53 mequivalents Nitrogen/g, 1.48 mequivalents Chloride/g of polymer resin.

EXAMPLE II

Preparation of the Ammonium Sulfide Polymer in its acetate form

The ammonium chloride of Example I (3 g) was stirred with 1 N NaOH (100 ml) for 3 hours, filtered and washed three times successively with methylene chloride (50 ml) then ethanol (50 ml). The resultant resin was dried overnight at 23° C./20 mM to afford 2.7 g of a yellow product which analysed for C, 73.39; H, 8.83; N, 1.90; S, 4.78, Cl, 3.08. This analysis indicates 1.36 mequivalents Nitrogen/g, 1.49 mequivalents Sulfur/g, and 0.88 mequivalents Chlorine/g of polymer resin.

The yellow product above was washed with 10% aqueous acetic acid (100 ml) then three times successively with methylene chloride (40 ml) followed by ethanol (40 ml). The resultant white product was dried at 23° C./20 mM to afford Example II as the acetate 2.7 g.

The following Examples demonstrate the use of various insoluble quaternary ammonium containing compounds to stabilize various radiolabeled compounds. The analytical method employs liquid chromatography for separation followed by post column radioactivity quantitization.

EXAMPLE III-V

The following examples detail the storage of tritium-labeled methionine in aqueous ethanol solution with an initial radiochemical purity of 98% with the stabilizers of Examples I and II. The average change in purity is based upon three individual determinations.

| Ex. | Stabilizer | Number of Days Stored | Average Change in Purity (%) | Molar Excess |
|---|---|---|---|---|
| | None | 47 | 6 | |
| | | 62 | 11 | |
| | | 87 | 13 | |
| | | 118 | 19 | |
| III | Compound of Ex. I | 47 | 1 | |

| Ex. | Stabilizer | Number of Days Stored | Average Change in Purity (%) | Molar Excess |
|---|---|---|---|---|
| | | 62 | 3 | $1.2 \times 10^3$ of Sulfur and Nitrogen |
| | | 87 | 4 | |
| | | 118 | 11 | |
| IV | Compound of Ex. I | 48 | 0 | $8.7 \times 10^3$ of Sulfur and Nitrogen |
| | | 62 | 0 | |
| | | 87 | 0 | |
| | | 119 | 3 | |
| V | Compound of Ex. II | 47 | 2 | $1.2 \times 10^3$ of Sulfur and Nitrogen |
| | | 62 | 4 | |
| | | 87 | 5 | |
| | | 118 | 12 | |

EXAMPLE VI

An aqueous solution of tritium-labeled methionine having an initial purity of 93% was divided into equal parts. One part was stored without any stabilizer, while the other part was stored over $4.5 \times 10^3$ molar excess of the compound of Example I. After 36 days the change in radiochemical purity was 75% and 12% respectively. After 66 days the change in radiochemical purity was 85% and 19% respectively, and the biological activity of the two solutions was tested by attempting to use the stored solutions for protein translation. The solution of methionine stored without any stabilizer failed to translate effectively, whereas the solution stored over stabilizer underwent efficient protein translation.

| Ex. | Stabilizer Reagent | No. of Days | Change In Radiochemical Purity (%) | Molar Excess |
|---|---|---|---|---|
| | None | 36 | 75 | |
| | | 66 | 85 | |
| VI | Compound of Ex.1 | 36 | 12 | $4.5 \times 10^3$ of sulfur and Nitrogen |
| | | 66 | 19 | |

EXAMPLES VII AND VIII

Example VII and VIII illustrate the use of the present invention with the stabilizer of Example I and polystyrenedivinyl benzene copolymer substituted by triethyl ammonium with chloride as the counterion (TEAC) to stabilize a solution of tritium labeled lysine with a starting purity of 98.5%.

| Ex. | Stabilizer | Number of Days Stored | Change in Purity (%) | Molar Excess |
|---|---|---|---|---|
| | None | 34 | 3.0 | |
| | | 70 | 6.0 | |
| VII | TEAC | 34 | 0.5 | $1.5 \times 10^3$ of Sulfur and Nitrogen |
| | | 70 | 1.5 | |
| VIII | Compound of Ex. 1 | 34 | 0.5 | $1.5 \times 10^3$ of Sulfur and Nitrogen |
| | | 70 | 1.5 | |

EXAMPLES IX-XII

Examples IX-XII illustrate the use of the present invention to stabilize a radiolabeled nucleoside, tritium-labeled thymidine. Example IX and X employ the stabilizer of Example I, whereas Examples XI and XII employ a commercially available polystyrenedivinyl benzene copolymer anion exchange resin to which has been bound a trimethyl ammonium group with chloride as the counterion (TMAC) in accordance with the present invention.

| Ex. | Stabilizer Reagent | Change in Number of Days Stored | Radiochemical Purity (%) | Molar Excess |
|---|---|---|---|---|
|  | None | 14 | 3 |  |
|  |  | 22 | 7 |  |
|  |  | 29 | 7 |  |
| IX | Compound of Ex. 1 | 14 | 0 | $10^4$ Nitrogen and Sulfur |
|  |  | 22 | 5 |  |
|  |  | 29 | 3 |  |
| X | Compound of Ex. 1 | 14 | 0 | $2 \times 10^4$ Nitrogen and Sulfur |
|  |  | 22 | 2 |  |
|  |  | 29 | 2 |  |
| XI | TMAC | 14 | 0 | $10^4$ Nitrogen |
|  |  | 22 | 1 |  |
|  |  | 29 | 2 |  |
| XII | TMAC | 14 | 0 | $2 \times 10^4$ Nitrogen |
|  |  | 22 | 3 |  |
|  |  | 29 | 1 |  |

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. As an article of manufacture, a kit comprising at least one container of solution of a radiolabeled organic compound and a substantially insoluble resin containing a quaternary ammonium group.

2. A kit as claimed in claim 1 wherein said radiolabeled compound is a radiolabeled amino acid.

3. A kit as claimed in claim 2 wherein said radiolabeled amino acid is methionine or leucine.

4. A kit as claimed in claim 1 wherein the quaternary ammonium is substituted by lower alkyl.

5. A kit comprising at least one container of solution of a radiolabeled compound and a substantially insoluble quaternary ammonium substituted polystyrene-divinyl benzene copolymer.

6. A kit as claimed in claim 1 wherein the counterion of said resin containing a quaternary ammonium group is halide or a lower alkyl carboxylate anion.

7. A kit as claimed in claim 1 wherein said resin containing a quaternary ammonium group, in addition, contains a sulfide group.

8. A kit comprising at least one container of solution of a radiolabeled compound and a substantially insoluble polystyrene divinyl benzene ammonium sulfide.

9. A kit as claimed in claim 1 wherein the solvent of said solution is water, ethanol, a mixture of water and ethanol, benzene, hexane, a dilute mineral acid, or a dilute organic acid.

10. A kit as claimed in claim 1 wherein the radionuclide of said radiolabeled compound is tritium, carbon-14, phosphorus-32, phosphorus-33, sulfur-35, iodine-125, or iodine-131.

11. A method of stabilizing a solution of a radiolabeled organic compound comprising storing said solution in contact with a substantially insoluble resin containing a quaternary ammonium group.

12. A method as claimed in claim 11 wherein said radiolabeled compound is a radiolabeled amino acid.

13. A method as claimed in claim 12 wherein said radiolabeled amino acid is methionine.

14. A method as claimed in claim 11 wherein the quaternary ammonium is substituted by lower alkyl.

15. A method of stabilizing a solution of a radiolabeled compound comprising storing said solution in contact with a substantially insoluble quaternary ammonium substituted polystyrene-divinyl benzene copolymer.

16. A method as claimed in claim 11 wherein the counterion of said resin containing a quaternary ammonium group is halide or a lower alkyl carboxylate anion.

17. A method as claimed in claim 11 wherein said resin containing a quaternary ammonium group, in addition, contains a sulfide group.

18. A method of stabilizing a solution of a radiolabeled compound comprising storing said solution in contact with a substantially insoluble polystyrene divinyl benzene ammonium sulfide.

19. A method as claimed in claim 11 wherein the solvent of said solution is water, ethanol, a mixture of water and ethanol, benzene, hexane, a dilute mineral acid, or a dilute organic acid.

20. A method as claimed in claim 11 wherein the radionuclide of said radiolabeled compound is tritium, phosphorus-32, phosphorus-33, carbon-14, sulfur-35, iodine-125, or iodine-131.

21. A compound for stabilizing a solution of a radiolabeled organic compound comprising a substantially insoluble resinous substrate having pendant quaternary ammonium and sulfide groups.

22. A compound for stabilizing a solution of a radiolabeled compound comprising storing said solution in contact with a substantially insoluble polystyrene-divinyl benzene copolymer, having pendant quaternary ammonium and sulfide groups.

23. A compound as claimed in claim 21 wherein said quaternary ammonium group is substituted by lower alkyl.

24. A compound as claimed in claim 23 wherein said alkyl group contains from one to five carbon atoms.

25. A compound as claimed in claim 21 wherein the counterion of said quaternary ammonium group is a halide or a lower alkyl carboxylate anion.

26. A compound as claimed in claim 25 wherein said counterion is chloride.

27. A compound as claimed in claim 21 wherein said sulfide group is substituted by lower alkyl.

28. Polystyrene-divinylbenzene ammonium sulfide chloride.

29. Polystyrene-divinylbenzene ammonium sulfide acetate.

30. A method of making the compounds claimed in claim 21 comprising reacting an alkyl thiol and an trialkylamine with a substantially insoluble substrate having a reactive site.

31. A composition comprising a solution of a radiolabeled organic compound, said solution being maintained in contact with a substantially insoluble resin containing a quaternary ammonium group.

32. A composition as claimed in claim 31 wherein said radiolabeled compound is a radiolabeled amino acid.

33. A composition as claimed in claim 32 wherein said radiolabeled amino acid is methionine or leucine.

34. A composition as claimed in claim 31 wherein the quaternary ammonium group is substituted by lower alkyl.

35. A composition comprising a solution of a radiolabeled compound, said solution being maintained in contact with a substantially insoluble quaternary ammonium substituted polystyrene-divinyl benzene copolymer.

36. A composition as claimed in claim 31 wherein the counterion of said resin containing a quaternary ammonium group is halide or a lower alkyl carboxylate anion.

37. A composition as claimed in claim 31 wherein said resin containing a quaternary ammonium group, in addition, contains a sulfide group.

38. A composition as claimed in claim 37 wherein said resin containing a quaternary ammonium and a sulfide group is a polystyrene divinyl benzene ammonium sulfide.

39. A composition as claimed in claim 31 wherein the solvent of said solution is water, ethanol, a mixture of water and ethanol, benzene, hexane, a dilute mineral acid, or a dilute organic acid.

40. A composition as claimed in claim 31 wherein the radionuclide of said radiolabeled compound is tritium, carbon-14, phosphorus-32, phosphorus-33, sulfur-35, iodine-125 or iodine-131.

* * * * *